US005664340A

United States Patent [19]
Brown

[11] Patent Number: 5,664,340
[45] Date of Patent: Sep. 9, 1997

[54] ULTRAVOILET, ANTIBACTERIAL, ANTIFUNGAL DRYERLIGHT

[76] Inventor: Clay A. Brown, P.O. Box 607, Calhoun, La. 71225

[21] Appl. No.: 619,943

[22] Filed: Mar. 18, 1996

[51] Int. Cl.$^6$ .................................................. F26B 3/34
[52] U.S. Cl. .................................................. 34/275; 34/595
[58] Field of Search .......................... 34/275, 278, 595, 34/602, 611

[56] References Cited

U.S. PATENT DOCUMENTS

| D. 358,637 | 5/1995 | Boehme | D23/364 |
|---|---|---|---|
| 3,803,725 | 4/1974 | Takeyama | 34/595 |
| 3,877,152 | 4/1975 | Gorman | 34/275 |
| 3,975,790 | 8/1976 | Patterson | 15/339 |
| 4,182,050 | 1/1980 | Righi | 34/275 |
| 5,160,699 | 11/1992 | Siegal | 422/24 |
| 5,233,723 | 8/1993 | Hung | 15/339 |
| 5,343,629 | 9/1994 | Rae | 34/278 |

*Primary Examiner*—John M. Sollecito
*Assistant Examiner*—Steve Gravini
*Attorney, Agent, or Firm*—John D. Gugliotta; David L. Volk

[57] ABSTRACT

A U.V. Anti-Bacterial, Anti-Fungal Dryer Light is provided designed to eliminate bacteria and fungus-causing germs from the laundry. The present invention consists of ultraviolet mechanisms situated within the door of typical gas and electric dryers thereby eliminating germs from the laundered clothing. Ultraviolet lights are contained within a dryer door-mounted plate and covered with clear glass or polycarbonate plastic. When the dryer is on, the ultraviolet lights will illuminate, thus beginning the process of abolishing the germs of the laundry.

11 Claims, 2 Drawing Sheets

5,664,340

ULTRAVOILET, ANTIBACTERIAL, ANTIFUNGAL DRYERLIGHT

BACKGROUND OF THE INVENTION

1. Field of the Invention

The present invention relates generally to sterilizers and, more particularly, to a sterilizer used in combination with a clothes dryer for eliminating the growth of bacterial and fungus therein.

2. Description of the Related Art

In the related art, dryers utilizing ultraviolet radiation are known. For example, in U.S. Pat. No. 5,343,629, issued in the name of Rae, a UV dryer is disclosed for use in drying photopolymerisable inks on paper.

Also, in U.S. Pat. No. 5,160,699, issued in the name of Siegal, a germicidal apparatus is disclosed having an enclosed sanitizing cabinet for exposing eyewear articles to ultraviolet radiation. Such is used for sterilizing eyewear articles.

Also generally known in the related art are household appliances which utilize ultraviolet radiation for sterilization purposes. An example appears in U.S. Pat. No. 5,233,723, issued in the name of Hung, in which a sterilizing vacuum cleaner is disclosed which is utilized to sterilize the air passing through the vacuum.

Although such various methods of utilizing ultraviolet radiation for sterilization purposes exist, to date no such method has been adapted for use with a clothes dryer in order to provide elevated levels of hygiene and cleanliness. Consequently, a need has been felt for providing such an apparatus which can be utilized with conventional clothes dryers.

SUMMARY OF THE INVENTION

It is therefore an object of the present invention to provide an improved device for sterilizing and drying cloths.

It is a further object of the present invention to provide a device for sterilizing cloths utilizing an otherwise conventional clothes dryer.

It is another object of the present invention to provide a device for sterilizing clothes in a manner that reduces the amount of detergent and bleach necessary to sanitize cloths.

It is a feature of the present invention to provide an improved clothes dryer device which incorporates a germicidal, ultraviolet lamp for applying sterilizing ultraviolet radiation to the clothes as they dry.

In accordance with a preferred embodiment, a U.V. Anti-Bacterial, Anti-Fungal Dryer Light is provided designed to eliminate bacteria and fungus-causing germs from the laundry. Wet clothes being the perfect breeding ground for bacteria and fungus, the present invention provides those who use it with added protection from germs found in laundry. Adaptable for use with consumer appliances, industrial and commercial dryers can also employ this dryer accessory. For example, a hospital can utilize the present invention to further protect their patients.

The present invention consists of ultraviolet mechanisms situated within the door of typical gas and electric dryers thereby eliminating germs from the laundered clothing. Used in other applications for the same "bacteria-killing" purpose, these lights are contained within the dryer door-mounted plate and covered with clear glass or polycarbonate plastic. When the dryer is on, the ultraviolet lights will illuminate, thus beginning the process of abolishing the germs of the laundry.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
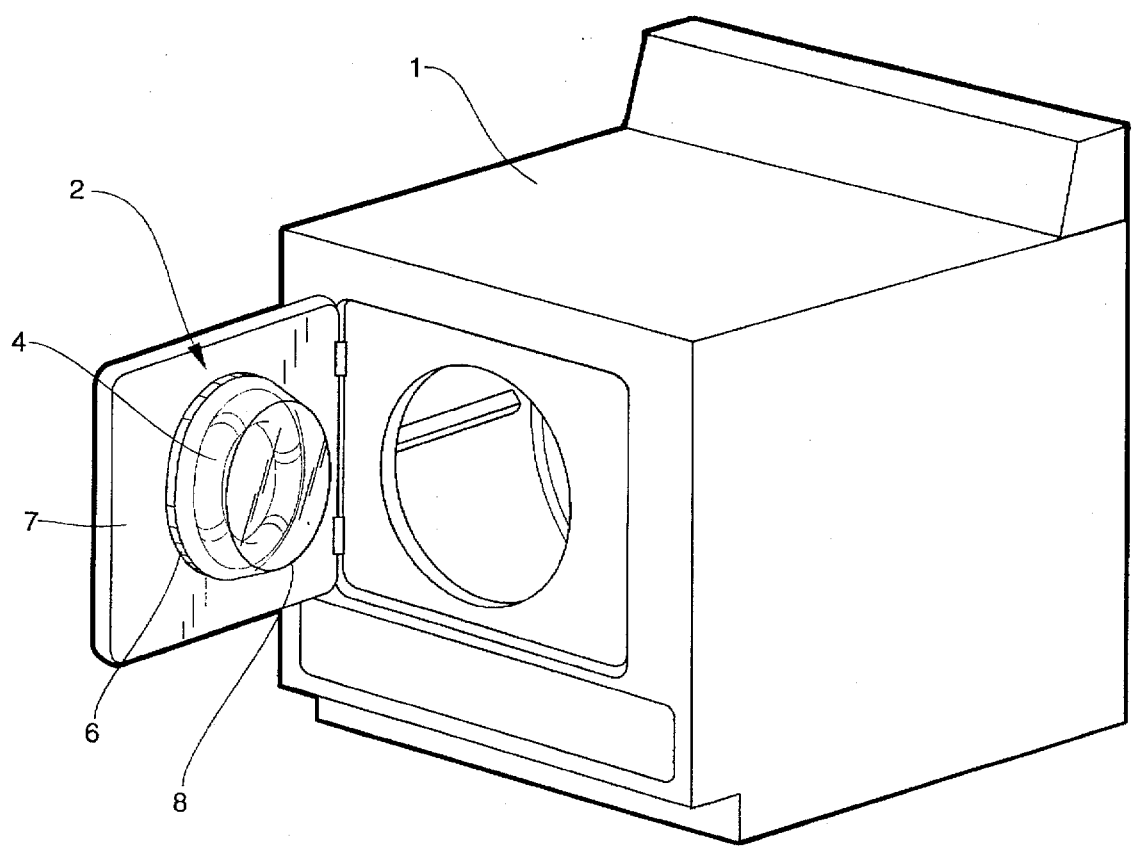
FIG. 1 is an orthographic view of a clothes dryer utilizing an ultraviolet, antibacterial, antifungal dryer light system according to the preferred embodiment of the present invention.
Figure 2:
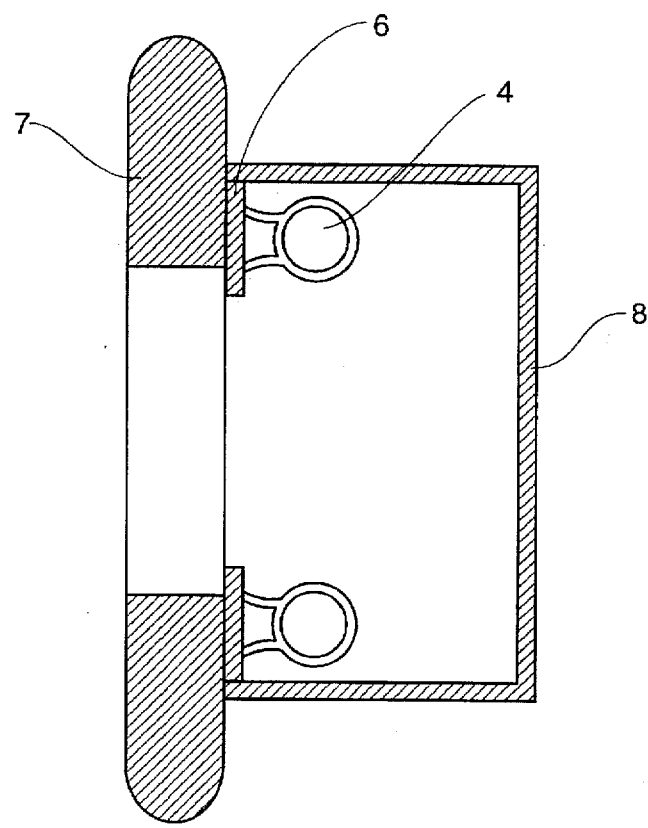
FIG. 2 is a cross sectional side view of the door portion of the dryer referred to in FIG. 1.

Referring now to FIG. 1 and FIG. 2, a conventional clothes dryer 1 is provided utilizing an ultraviolet, antibacterial, antifungal dryer light system, generally noted as 2, according to the preferred embodiment of the present invention. An ultraviolet light 4 is provided designed to eliminate bacteria and fungus-causing germs from the laundry. As shown in FIG.1 and FIG. 2, the ultraviolet light 4 may be ring-shaped. A mounting bracket 6 affixes the light 4 to the door 7 of the dryer 1 such that the ultraviolet light 4 is within the dryer 1 when the door 7 is shut. The light 4 is covered with clear impact shield 8 made of glass or polycarbonate plastic. When the dryer is on, the ultraviolet lights 4 illuminate, thus beginning the process of killing the germs of the laundry.

Figure 3:
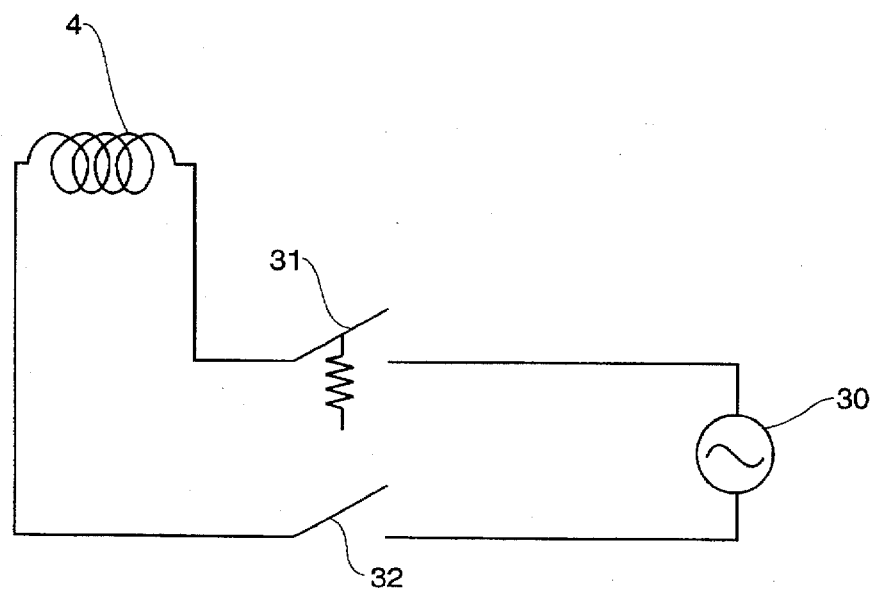
FIG. 3 is an electrical schematic of the ultraviolet, antibacterial, antifungal dryer light system according to the preferred embodiment of the present invention.

Referring to FIG. 3, a power means 30 envisioned as a standard 120 volt or 240 volt household power supply is provided to power the lamp 4. It is envisioned that this power means 30 would be drawn from the operating power of the dryer 1. A first control switch 31 is envisioned as manually initiating the operation of the lamp 4, and a second control switch 32 is envisioned as interlocking the operation of the lamp 4 with the status of the dryer door 7, i.e. operation of the lamp 4 would only be permitted if the door 7 is in a closed position.

2. Operation of the Preferred Embodiment

With reference to the figures described above, to use the present invention, the user places clothes in the dryer's drum for both drying and exposure to the U.V. light. The proper drying cycle is selected, and the dryer is energized in a conventional manner. While the clothes are drying, the U.V. light 4 are illuminated, thereby radiating the inside of the dryer's drum and exposing the clothing to the germicidal effects of the U.V. lights. Bacteria and fungi are thereby killed.

When the drying cycle is completed, the clothing can be removed for proper distribution and handling.

The foregoing description is included to illustrate the operation of the preferred embodiment and is not meant to limit the scope of the invention. From the foregoing description, many variations will be apparent to those skilled in the art that would yet be encompassed by the spirit and scope of the invention. While a preferred embodiment of the present invention has been shown and described, it will be understood that it is not intended to limit the disclosure, but rather it is intended to cover all modifications and alternate constructions falling within the spirit and scope of the invention as defined in the appended claims.

What is claimed is:

1. An apparatus for killing bacteria and fungus-causing germs on clothing, said apparatus comprising:

a clothes dryer, said clothes dryer of a conventional type having a door and a drying drum;

the door having a drum-facing surface;

ultraviolet light means comprising an U.V. light;

said ultraviolet light means positioned on said drum-facing surface of said door such that said U.V. light is within said dryer drum, said U.V. light for illuminating said dryer drum with germicidal ultraviolet radiation.

2. The apparatus as described in claim 1, wherein said ultraviolet light means further comprises:

a dryer door mounting plate affixed to said drum-facing surface of said dryer door;

said U.V. light mounted to said mounting plate; and a cover for protecting said U.V. light from direct physical contact with contents of said dryer.

3. The apparatus as described in claim 2, wherein said cover is manufactured from clear glass.

4. The apparatus as described in claim 2, wherein said cover is manufactured from clear polycarbonate plastic.

5. An ultraviolet, antibacterial, antifungal dryer light system for use with a conventional clothes dryer having a door and a drying drum, said door having a dram-facing surface, said system comprising:

a germicidal ultraviolet light designed to eliminate bacteria and fungus-causing germs;

a mounting bracket affixed to the drum-facing surface of the door of the dryer, said mounting bracket supporting said light such that said light is within said drum;

an impact shield attached to said mounting bracket and covering said light, said shield for protecting said light from direct physical contact with contents of said dryer;

power means for providing electrical power to said light;

a first control switch in communication with said light for manually initiating the operation of said light; and a second control switch in communication with both said light and said door, said second control switch for permitting the operation of said lamp only upon the sensing of said door in a closed position.

6. The apparatus as described in claim 5, wherein said cover is manufactured from clear glass.

7. The apparatus as described in claim 5, wherein said cover is manufactured from clear polycarbonate plastic.

8. A germicidal dryer light system for use with a conventional clothes dryer having a door and a drum, the door having a drum-facing surface, the system comprising:

a germicidal ultraviolet light affixed to the drum-facing surface of the door such that said light is within said drum; and an impact shield positioned to cover the light for protecting the light from direct physical contact with contents of the dryer.

9. The germicidal dryer light system of claim 8, further comprising a power means for providing electrical power to the light and at least one switch for initiating operation of the light.

10. The germicidal dryer light system of claim 8, wherein the light is ring-shaped and the shield circumferentially surrounds the light.

11. The germicidal dryer light system of claim 10, wherein the shield is configured to permit ultraviolet radiation from the light to transmit through a portion of the shield which circumferentially surrounds the light.

* * * * *